(12) United States Patent
Sabo et al.

(10) Patent No.: US 8,494,607 B2
(45) Date of Patent: Jul. 23, 2013

(54) HANDHELD DIABETES MANAGEMENT DEVICE HAVING A DATABASE MANAGEMENT SYSTEM

(75) Inventors: Robert P. Sabo, Indianapolis, IN (US); Robert Timmerman, Fishers, IN (US); Mark Nierzwick, Brownsburg, IN (US); Robert E. Reinke, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 246 days.

(21) Appl. No.: 12/905,475

(22) Filed: Oct. 15, 2010

(65) Prior Publication Data
US 2012/0095314 A1    Apr. 19, 2012

(51) Int. Cl.
*A61B 5/05* (2006.01)

(52) U.S. Cl.
USPC ............ 600/345; 600/347; 600/365; 707/737

(58) Field of Classification Search
USPC .......................... 600/306, 319, 345–347, 365
See application file for complete search history.

(56) References Cited

U.S. PATENT DOCUMENTS

| | | | | |
|---|---|---|---|---|
| 5,960,403 | A | * | 9/1999 | Brown .............................. 705/2 |
| 7,024,236 | B2 | * | 4/2006 | Ford et al. ..................... 600/345 |
| 2003/0208454 | A1 | * | 11/2003 | Rienhoff et al. .................. 707/1 |

FOREIGN PATENT DOCUMENTS

| | | |
|---|---|---|
| WO | 2009/026946 | 3/2009 |
| WO | 2009/081404 | 7/2009 |

OTHER PUBLICATIONS

"Flash File System" Sep. 13, 2010, XP55013819, Wikipedia.
"Error Detection and Correction" Sep. 1, 2010, XP55013814, Wikipedia, section "Error-correcting code".

* cited by examiner

*Primary Examiner* — Patricia Mallari
*Assistant Examiner* — Michael D'Angelo
(74) *Attorney, Agent, or Firm* — Harness, Dickey (57) ABSTRACT

A handheld diabetes management device having a database management system is disclosed. The device comprises a plurality of input modules, including a blood glucose reader, a user interface, a communications interface, and a continuous blood glucose input module. The input modules output data used to generate data records of different record types. The device further comprises N databases, each database having a different frequency range associated thereto, wherein the new record is stored in a particular database of the N databases based on the frequency range of the particular database and the frequency of the particular record type, and N is an integer greater than 1. The device further includes a database operation module that performs database operations on the N databases. The database management system provides increased reliability in the keeping of records on which medically important decisions are made.

15 Claims, 8 Drawing Sheets

Table 1 - DM Result

```
<column>
    Date-year: char(1)
    Date-month: char(1)
    Date-day: char(1)
    Time-hours: char(1)
    Time-minutes: char(1)
    Test Flags: char(1)
    bG Concentration: int
    Record Count: int
    DM Record Contents: char(1)
    Mealtime Selection: char(1)
    Health Event Selection: char(1)
    Recommended Carb Amount: int
    Modified Carb Amount: int
    Meal Name: text
    Food Item 1: text
    Food Item 2: text
    Food Item 3: text
    Food Item 4: text
    Food Item 5: text
    Food Item 6: text
    Food Item 7: text
    Food Item 8: text
    Food Item 9: text
    Food Item 10: text
    Food Item 11: text
    Food Item 12: text
    Recommended Bolus Insulin Amount for bG correction: int
    Recommended Bolus Insulin Amount for meal rise: int
    Confirmed Bolus Insulin Amount for bG correction: int
    Confirmed Bolus Insulin Amount for meal rise: int
    Bolus Insulin Amount for bG correction: int
    Basal Insulin Amount for meal rise: int
    Insulin Delivery Method: int
    Recommended Bolus based on carbs: int
    Recommended Bolus based on health: int
    Recommended Bolus based on bG: int
    Active Insulin: int
    Bolus Advice Minimum bG value (LTR): int
    Bolus Advice Maximum bG value (UTR): int
    Carb Ratio Insulin value: int
    Carb Ratio Carb value: int
    Insulin Sensitivity Insulin value: int
    Insulin Sensitivity bG value: int
    Bolus Advice Flags: int
    Health percentage: int
    Bolus Advice Meal Excursion: int
    Bolus Advice Active Time Out: int
    Bolus Advice Snack Limt (snack size): int
    Carb Calculated Amount: int
    Bolus Advice Offset Time Out: int
    Bolus Advice Upper bG Limit: int
    Carb Ratio Carbs Calculated Amount: int
    Offset Time: bigint
    16-Bit CRC: int
```

FIG. 7A

Table 2 - Error

\<column\>
- Date-year: binary(8)
- Date-month: binary(8)
- Date-day: binary (8)
- Time-hours: binary(8)
- Time-minutes: binary(8)
- Error-Code: binary(16)
- Error-Description: text
- 16-Bit CRC: binary(16)

720

Table 3 - DM cG Result

\<column\>
- Date-year: (binary(8)
- Date-month: binary(8)
- Date-day: binary(8)
- Time-hours: binary(8)
- Time-minutes: binary(8)
- Test Flag: binary(8)
- Concentration: binary(16)
- Record Count: binary(16)
- 16-Bit CRC: binary(16)

730

Table 4 - Pump

\<column\>
- Date-year: binary(8)
- Date-month: binary(8)
- Date-day: binary(8)
- Time-hours: binary(8)
- Time-minutes: binary(8)
- Time-seconds: binary(8)
- Event Date: binary(32)
- Event ID: binary(16)
- Event Data Checksum: binary(16)
- Event Counter: binary(32)
- Event Counter Checksum: binary(32)
- Gap Event: binary(8)
- Synch Flag: binary(8)
- 16-Bit CRC: binary(16)

Table 5 - Bolus Advice Correction

```
<column>
    Active Flag: binary(8)
    bG Result Date Year: binary(8)
    bG Result Date Month: binary(8)
    bG Result Date Day: binary(8)
    bG Result Date Hour: binary(8)
    bG Result Date Minute: binary(8)
    Correct Start Date Year: binary(8)
    Correct Start Date Month: binary(8)
    Correct Start Date Day: binary(8)
    Correct Start Date Hour: binary(8)
    Correct Start Date Minute: (binary(8)
    Correct End Date Year: binary(8)
    Correct End Date Month: binary(8)
    Correct End Date Day: binary(8)
    Correct End Date Minute: binary(8)
    Correction Offset Time: binary(16)
    Correction Active Time: binary(16)
    Correction Upper bG Limit: binary(16)
    Delta bG: binary(32)
    Correction Bolus: binary(32)
    bG Result Record Counter: binary(16)
    Meal Correction Active Flag: binary(8)
    Meal Increase: binary(16)
    DM Record Contents: binary(8)
    Mealtime Selection: binary(8)
    Test Flags: binary(8)
    Bolus Advice Flags: binary(8)
    Concentration: binary(16)
    Carb Amount: binary(16)
    Bolus Insulin Amount: binary(16)
    Spare: binary(8)
    16-Bit CRC: binary(16)
```

Table 6 - Food

```
<column>
    Description: text
    Category: text
    Food_Flags: binary(8)
    carbs: binary(16)
    fats: binary(16)
    protein: binary(16)
    fiber: binary(16)
    calories: binary(16)
    Serving Size: binary(16)
    Spare: binary(16)
    16-Bit CRC: binary(16)
```

FIG. 7C

HANDHELD DIABETES MANAGEMENT DEVICE HAVING A DATABASE MANAGEMENT SYSTEM

FIELD

The present disclosure relates to a system for managing a plurality of databases on a handheld diabetes management device.

BACKGROUND

Medical devices are often used as diagnostic devices and/or therapeutic devices in diagnosing and/or treating medical conditions of patients. For example, a blood glucose meter is used as a diagnostic device to measure blood glucose levels of patients suffering from diabetes. An insulin infusion pump is used as a therapeutic device to administer insulin to patients suffering from diabetes.

Diabetes mellitus, often referred to as diabetes, is a chronic condition in which a person has elevated blood glucose levels that result from defects in the body's ability to produce and/or use insulin. There are three main types of diabetes. Type 1 diabetes may be autoimmune, genetic, and/or environmental and usually strikes children and young adults. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. The incidence of diabetes is increasing rapidly, and it is estimated that between 2005 and 2030, the number of deaths from diabetes will double. In the United States, nearly 24 million Americans have diabetes, and an estimated 25% of seniors age 60 and older are affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Diabetes is managed primarily by controlling the level of glucose in the bloodstream. This level is dynamic and complex, and is affected by multiple factors including the amount and type of food consumed, and the amount of insulin (which mediates transport of glucose across cell membranes) in the blood. Blood glucose levels are also sensitive to exercise, sleep, stress, smoking, travel, illness, menses, and other psychological and lifestyle factors unique to individual patients. The dynamic nature of blood glucose and insulin and all other factors affecting blood glucose often require a person with diabetes to forecast blood glucose levels. Therefore, therapy in the form of insulin, oral medications, or both can be timed to maintain blood glucose levels in an appropriate range.

Management of diabetes is time-consuming for patients because of the need to consistently obtain reliable diagnostic information, follow prescribed therapy, and manage lifestyle on a daily basis. Diagnostic information such as blood glucose is typically obtained from a capillary blood sample with a lancing device and is then measured with a handheld blood glucose meter. Interstitial glucose levels may be obtained from a continuous glucose sensor worn on the body. Prescribed therapies may include insulin, oral medications, or both. Insulin can be delivered with a syringe, an ambulatory infusion pump, or a combination of both. With insulin therapy, determining the amount of insulin to be injected can require forecasting meal composition of fat, carbohydrates, and proteins along with effects of exercise or other physiological states. The management of lifestyle factors such as body weight, diet, and exercise can significantly influence the type and effectiveness of therapy.

Management of diabetes involves large amounts of diagnostic data and prescriptive data acquired in a variety of ways: from medical devices, from personal healthcare devices, from patient-recorded logs, from laboratory tests, and from healthcare professional recommendations. Medical devices include patient-owned bG meters, continuous glucose monitors, ambulatory insulin infusion pumps, diabetes analysis software. Each of these systems generates and/or manages large amounts of diagnostic and prescriptive data. Personal healthcare devices include weight scales, blood pressure cuffs, exercise machines, thermometers, and weight management software. Patient recorded logs include information relating to meals, exercise, and lifestyle. Lab test results include HbA1C, cholesterol, triglycerides, and glucose tolerance. Healthcare professional recommendations include prescriptions, diets, test plans, and other information relating to the treatment of the patient.

There is a need for a handheld device to aggregate, manipulate, manage, present, and communicate diagnostic data and prescriptive data from medical devices, personal healthcare devices, patient recorded information, biomarker information, and recorded information in an efficient manner. The handheld device can improve the care and health of a person with diabetes so that the person with diabetes can lead a full life and reduce the risk of complications from diabetes.

Additionally, to effectively manage the care and health of the patient, there is a need for the handheld device to store the diagnostic and prescriptive data on a database on the handheld device. A technical problem arises, however, when the database is stored on a nonvolatile solid-state memory, as the risk of a database failing increases. Thus, there is a need to reliably store medically important data in a database on a handheld device.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

In a first aspect of the disclosure, a handheld diabetes management device having a database management system is disclosed. The diabetes management device includes a blood glucose reader that receives a fluid sample from a patient and that outputs a blood glucose measurement that is used to generate a first record having a first record type, a user interface that receives input from a patient via an input device associated with the handheld diabetes management device and that outputs patient data that is used to generate a second record having a second record type, and a communication interface that receives data from an external device and that outputs device data that is used to generate a third record having a third record type. The first record type, the second record type, and the third record type are of a plurality of different record types, wherein each record type of the plurality of different record types has a corresponding frequency, wherein the frequency of a record type indicates an average amount of records having the record type received during a predetermined period of time. The handheld diabetes management device further comprises N databases, each database having a different frequency range associated thereto, wherein a new record of a particular record type based on data received from one of the blood glucose reader, the user interface, and the communication interface is stored in a particular database of the N databases based on the frequency range of the particular database and the frequency of the particular record type, and wherein N is an integer greater than 1. The handheld diabetes management device further includes a database operation module that performs database operations on the N databases.

In a second aspect of the disclosure, a handheld diabetes management device having a database management system is disclosed. The handheld diabetes management device includes a plurality of input modules, the plurality of modules including i) a blood glucose reader that receives a fluid sample from a patient and that outputs a blood glucose measurement that is used to generate a first record having a first record type, ii) a user interface that receives input from a patient via an input device associated with the handheld diabetes management device and that outputs patient data that is used to generate a second record having a second record type based, iii) a communication interface that receives data from an external device and that outputs device data that is used to generate a third record having a third record type, and iv) a continuous blood glucose input module that receives a blood glucose reading from a continuous blood glucose meter and that outputs a continuous blood glucose measurements used to generate a fourth record of a fourth record type. The first record type, the second record type, the third record type, and the fourth record type are of a plurality of different record types, wherein each record type of the plurality of different record types has a corresponding frequency, and wherein the frequency of a record type indicates an average amount of records having the record type received during a predetermined period of time. The handheld diabetes management device further comprises a record generation module that receives data from one or more of the input modules and generates a new record of a particular record type based on the received data. The handheld diabetes management device also includes N databases, each database having a different frequency range associated thereto, wherein the new record is stored in a particular database of the N databases based on the frequency range of the particular database and the frequency of the particular record type, and wherein N is an integer greater than 1. The handheld diabetes management device further includes a database operation module that performs database operations on the N databases.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

BRIEF DESCRIPTION OF THE DRAWINGS

FIGS. 7A-C show a set of exemplary tables that are stored in an exemplary diabetes management device.

Corresponding reference numerals indicate corresponding parts throughout the several views of the drawings. The drawings described herein are for illustrative purposes only of selected embodiments and not all possible implementations, and are not intended to limit the scope of the present disclosure.

DETAILED DESCRIPTION

Example embodiments will now be described more fully with reference to the accompanying drawings.

Figure 1:
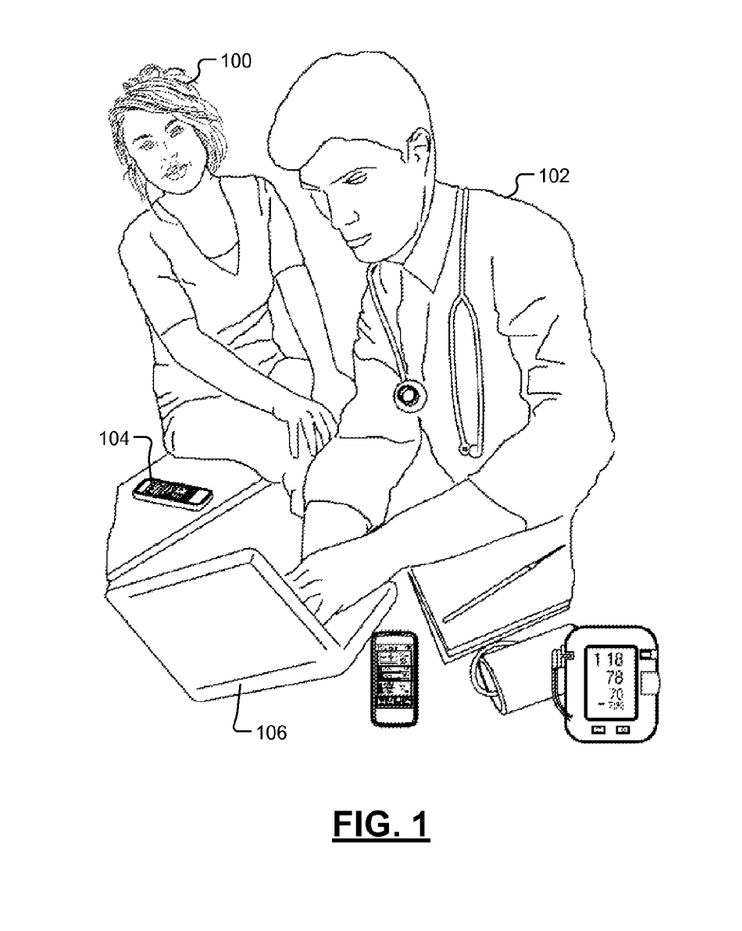
FIG. 1 shows a patient and a treating clinician.

Referring now to FIG. 1, a person 100 with diabetes and a healthcare professional 102 are shown in a clinical environment. Persons with diabetes include persons with metabolic syndrome, pre-diabetes, type 1 diabetics, type 2 diabetics, and gestational diabetics and are collectively referred to as a patient. Healthcare providers for diabetes are diverse and include nurses, nurse practitioners, physicians, and endocrinologists and are collectively referred to as a clinician.

During a healthcare consultation, the patient 100 typically shares with the clinician 102 a variety of patient data including blood glucose measurements, continuous glucose monitor data, amounts of insulin infused, amounts of food and beverages consumed, exercise schedules, and other lifestyle information. The clinician 102 may obtain additional patient data that includes measurements of HbA1C, cholesterol levels, triglycerides, blood pressure, and weight of the patient 100. The patient data can be recorded manually or electronically on a handheld diabetes management device 104, a diabetes analysis software executed on a personal computer (PC) 106, and/or a web-based diabetes analysis site (not shown). The clinician 102 can analyze the patient data manually or electronically using the diabetes analysis software and/or the web-based diabetes analysis site. After analyzing the patient data and reviewing adherence of the patient 100 to previously prescribed therapy, the clinician 102 can decide whether to modify the therapy for the patient 100.

Figure 2:
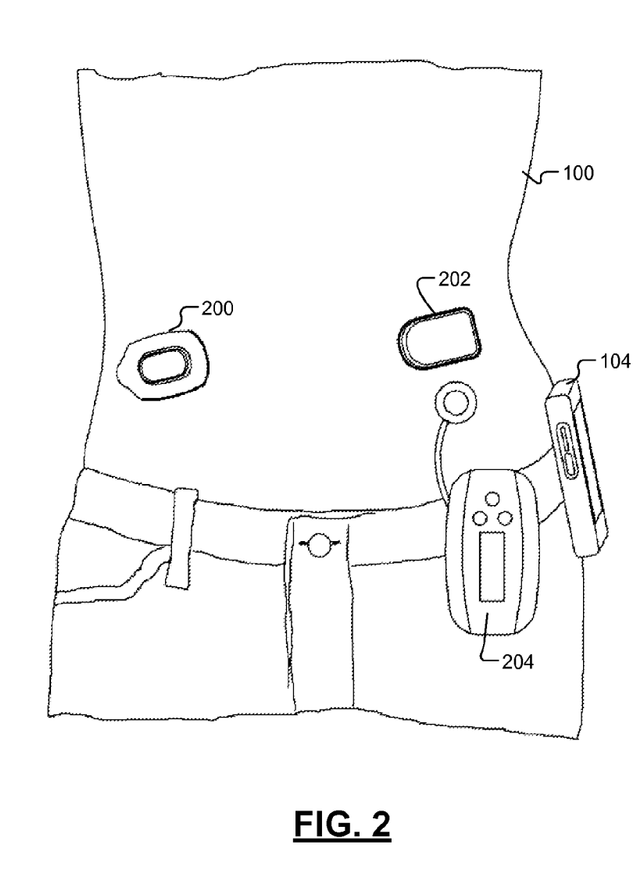
FIG. 2 shows a patient with a continuous glucose monitor (CGM), ambulatory durable insulin infusion pump, ambulatory non-durable insulin infusion pump, and diabetes manager.

Referring now to FIG. 2, the patient 100 can use a continuous glucose monitor (CGM) 200, an ambulatory durable insulin infusion pump 202 or an ambulatory non-durable insulin infusion pump 204 (collectively insulin pump 202 or 204), and the handheld diabetes management device 104 (hereinafter the diabetes manager 104). The CGM 200 uses a subcutaneous sensor to sense and monitor the amount of glucose in the blood of the patient 100 and communicates corresponding readings to the handheld diabetes management device 104.

The diabetes manager 104 performs various tasks including measuring and recording blood glucose levels, determining an amount of insulin to be administered to the patient 100 via the insulin pump 202 or 204, receiving patient data via a user interface, archiving the patient data, etc. The diabetes manager 104 periodically receives readings from the CGM 200 indicating insulin level in the blood of the patient 100. The diabetes manager 104 transmits instructions to the insulin pump 202 or 204, which delivers insulin to the patient 100. Insulin can be delivered in the form of a bolus dose, which raises the amount of insulin in the blood of the patient 100 by a predetermined amount. Additionally, insulin can be delivered in a scheduled manner in the form of a basal dose, which maintains a predetermined insulin level in the blood of the patient 100.

Figure 3:
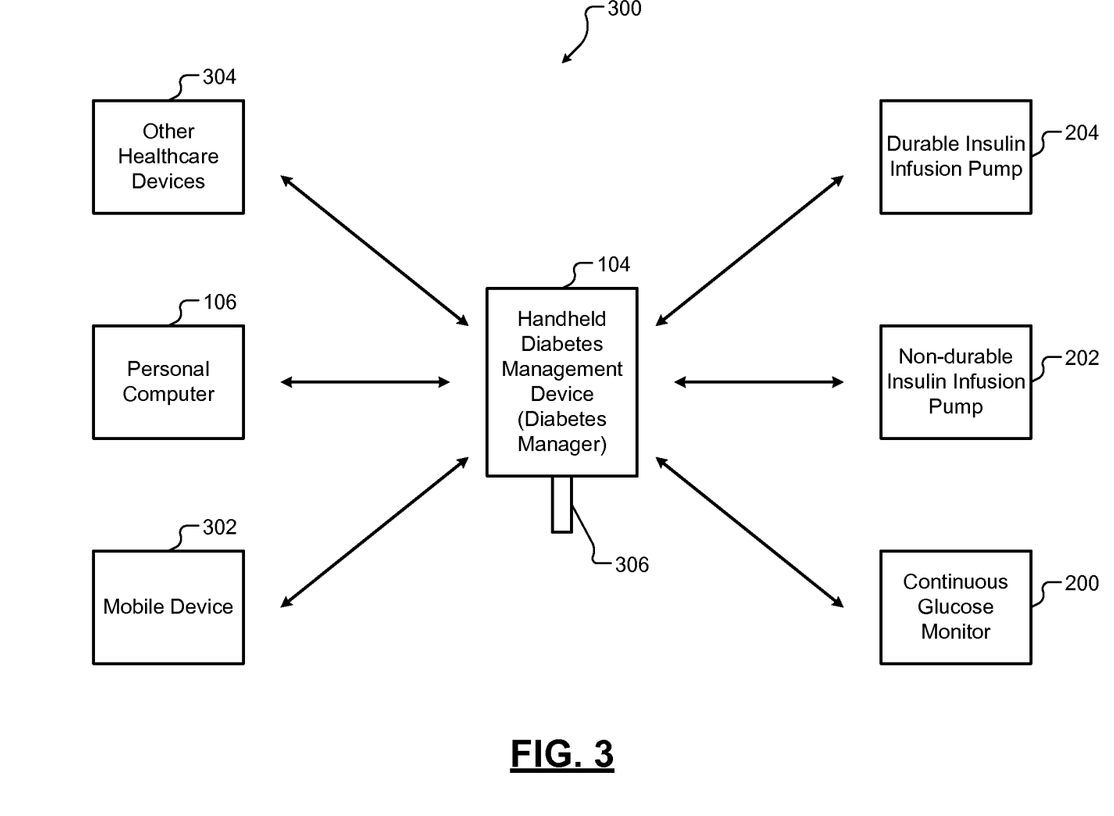
FIG. 3 shows a diabetes care system of systems used by patients and clinicians to manage diabetes.

Referring now to FIG. 3, a diabetes management system 300 used by the patient 100 and the clinician 102 includes one or more of the following devices: the diabetes manager 104, the continuous glucose monitor (CGM) 200, the insulin pump 202 or 204, a mobile device 302, the diabetes analysis software on the PC 106, and other healthcare devices 304. The diabetes manager 104 is configured as a system hub and communicates with the devices of the diabetes management system 300. Alternatively, the insulin pump 204 or the mobile device 302 can serve as the system hub. Communication between the various devices in the diabetes management system 300 can be performed using wireless interfaces (e.g., Bluetooth) and/or wireline interfaces (e.g., USB). Communication protocols used by these devices can include protocols compliant with the IEEE 11073 standard as extended using guidelines provided by Continua® Health Alliance Design Guidelines. Further, healthcare records systems such as Microsoft® HealthVault™ and Google™ Health can be used by the patient 100 and clinician 102 to exchange information.

The diabetes manager 104 can receive blood glucose readings from one or more sources (e.g., from the CGM 200). The CGM 200 continuously measures the blood glucose level of the patient 100. The CGM 200 periodically communicates the blood glucose level to the diabetes manager 104. The diabetes manager 104 and the CGM 200 communicate wirelessly using a proprietary Gazell wireless protocol developed by Nordic Semiconductor, Inc.

Additionally, the diabetes manager 104 includes a blood glucose meter (BGM) and a port that communicates with the BGM (both not shown). The port can receive a blood glucose measurement strip 306. The patient 100 deposits a sample of blood or other bodily fluid on the blood glucose measurement strip 306. The BGM analyzes the sample and measures the blood glucose level in the sample. The blood glucose level measured from the sample and/or the blood glucose level read by the CGM 200 can be used to determine the amount of insulin to be administered to the patient 100.

The diabetes manager 104 communicates with the insulin pump 202 or 204. The insulin pump 202 or 204 can be configured to receive instructions from the diabetes manager 104 to deliver a predetermined amount of insulin to the patient 100. Additionally, the insulin pump 202 or 204 can receive other information including meal and/or exercise schedules of the patient 100. The insulin pump 202 or 204 can determine the amount of insulin to administer based on the additional information.

The insulin pump 202 or 204 can also communicate data to the diabetes manager 104. The data can include amounts of insulin delivered to the patient 100, corresponding times of delivery, and pump status. The diabetes manager 104 and the insulin pump 202 or 204 can communicate using a wireless communication protocol such as Bluetooth. Other wireless or wireline communication protocols can also be used.

In addition, the diabetes manager 104 can communicate with other healthcare devices 304. For example, the other healthcare devices 304 can include a blood pressure meter, a weight scale, a pedometer, a fingertip pulse oximeter, a thermometer, etc. The other healthcare devices 304 obtain and communicate personal health information of the patient 100 to the diabetes manager 104 through wireless, USB, or other interfaces. The other healthcare devices 304 use communication protocols compliant with ISO/IEEE 11073 extended using guidelines from Continual® Health Alliance. The diabetes manager 104 can communicate with the other healthcare devices 304 using interfaces including Bluetooth, USB, etc. Further, the devices of the diabetes management system 300 can communicate with each other via the diabetes manager 104.

The diabetes manager 104 can communicate with the PC 106 using Bluetooth, USB, or other interfaces. A diabetes management software running on the PC 106 includes an analyzer-configurator that stores configuration information of the devices of the diabetes management system 300. The configurator has a database to store configuration information of the diabetes manager 104 and the other devices. The configurator can communicate with users through standard web or computer screens in non-web applications. The configurator transmits user-approved configurations to the devices of the diabetes management system 300. The analyzer retrieves data from the diabetes manager 104, stores the data in a database, and outputs analysis results through standard web pages or computer screens in non-web based applications.

The diabetes manager 104 can communicate with the mobile device 302 using Bluetooth. The mobile device 302 may include a cellular phone, a PDA, or a pager. The diabetes manager 104 can send messages to an external network through the mobile device 302. The mobile device 302 can transmit messages to the external network based on requests received from the diabetes manager 104.

Figure 4:
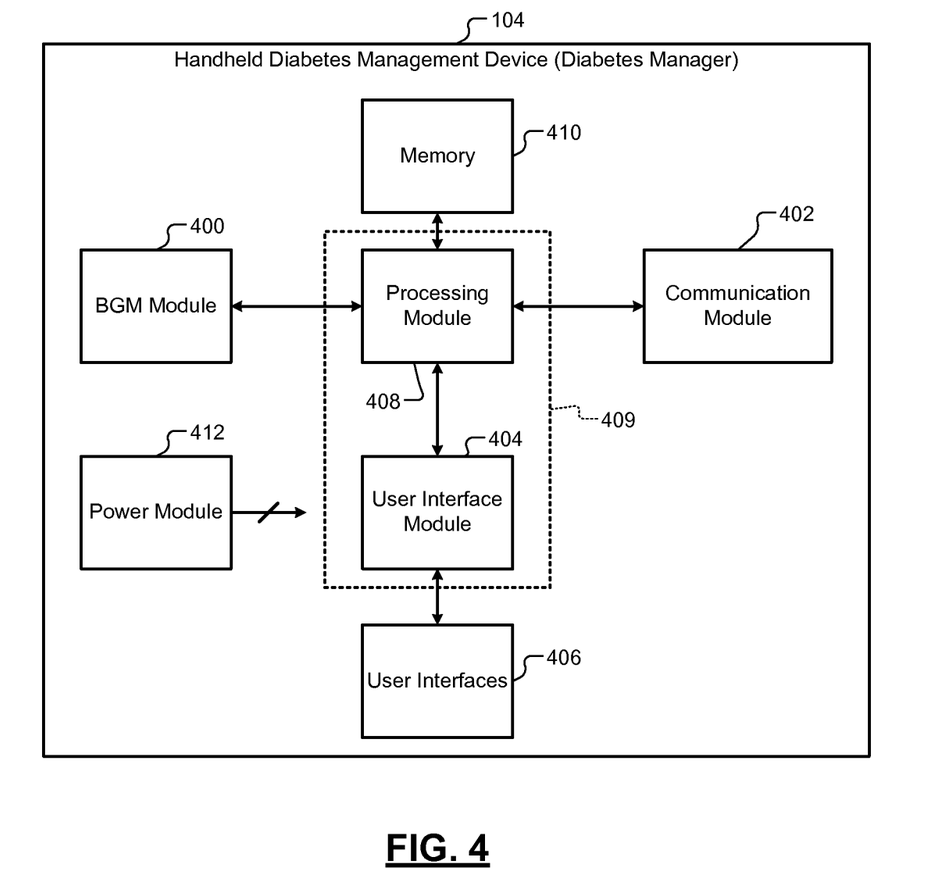
FIG. 4 shows a high level diagram of a diabetes care system-of-systems architecture.

Referring now to FIG. 4, the diabetes manager 104 comprises a blood glucose measuring (BGM) module 400, a communication module 402, a user interface module 404, user interfaces 406, a processing module 408, memory 410, and a power module 412. The BGM module 400 includes a blood glucose measuring engine that analyzes the sample provided by the patient 100 on the blood glucose measuring strip 306 and that measures the amount of blood glucose in the sample. The communication module 402 includes multiple radios that communicate with different devices of the diabetes management system 300. The user interface module 404 interfaces the diabetes manager 104 to various user interfaces 406 that the patient 100 can use to interact with the diabetes manager 104. For example, the user interfaces 406 can include keys, switches, a display, a speaker, a microphone, a secure digital (SD) card port, a USB port, etc. of the diabetes manager 104 (not shown).

The processing module 408 processes data received from the BGM module 400, the communication module 402, and the user interface module 404. The processing module 408 uses memory 410 for processing and storing data. The memory 410 can include volatile and nonvolatile memory. In some embodiments, the nonvolatile memory is solid state memory such as flash memory. The processing module 408 outputs data to and receives data from the user interfaces 406 via the user interface module 404. The processing module 408 outputs data to and receives data from the devices of the diabetes management system 300 via the communication module 402. The power module 412 supplies power to the components of the diabetes manager 104. The power module 412 includes a rechargeable battery. The battery can be recharged using an adapter that plugs into a wall outlet. The battery can also be charged via the USB port of the diabetes manager 104.

Figure 5:
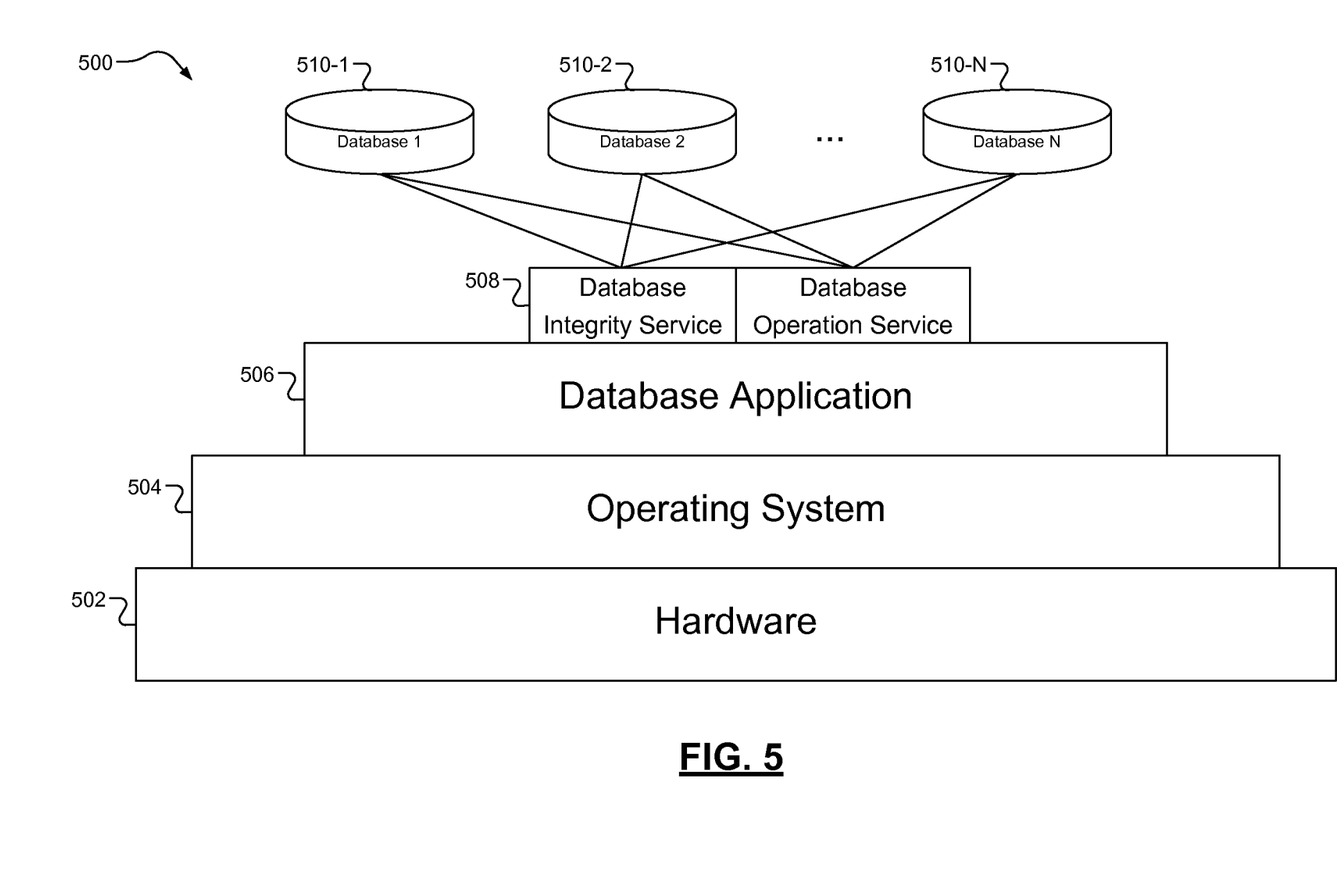
FIG. 5 shows a diagram of an exemplary hierarchy of a diabetes management device.

FIG. 5 shows an exemplary hierarchy 500 of a data management system that is implemented on the diabetes manager 104 (FIG. 1). A hardware level 502 represents hardware components of the diabetes manager 104. In an exemplary embodiment, the hardware components may include the components shown in FIG. 4. An operating system level 504 represents the operating system (OS) running on the diabetes manager 104. At the operating system level 504, an OS is responsible for managing the hardware components of the diabetes manager and to support software applications running on the diabetes manager 104. In an exemplary embodiment, the operating system of the diabetes manager can be Microsoft Windows CE®. It is envisioned, however, that another OS may be implemented at the OS level 504.

The OS supports a data management system of the diabetes manager. As shown in FIGS. 2 and 3, the diabetes manager is configured to receive data from a plurality of different devices. For instance, the diabetes manager may receive data records from a bG reader, a CGM, and an insulin pump, all of which are stored in a system of databases stored, which reside on the memory of the diabetes manager. Thus, the next level in the exemplary hierarchy 500 is a database application layer 506. In an exemplary embodiment, the database application is Microsoft SQL CE®. It is envisioned, however, that other database applications may be implemented on the diabetes manager.

To support the database, a set of database services reside at the service level 508 of the hierarchy. As will be discussed in greater detail below, the diabetes manager has a system of N databases 510-1, 510-2, ..., 510-N. The database services can include a database integrity service, which verifies the integrity of one or more of the N databases, and a database operation service, which performs various operations on the database. Exemplary database operations include creating, deleting, updating, and indexing the various databases.

As discussed with respect to FIG. 4, a handheld diabetes manager 400 may incorporate a non-volatile solid state memory, (e.g., a flash drive), as the primary storage device. A technical problem arises when a database is stored on a non-volatile solid state memory as opposed to hard disk memory. Namely, the probability that a record in the database will become corrupted, (i.e., the database will fail), increases when the database is stored on the non-volatile solid state memory. Moreover, as the frequency of updating and/or indexing the database increases, so does the probability that the database will fail. Given that the diabetes manager is used to assist a patient in his or her diabetes management, e.g., how much insulin to deliver to a patient, and the data used to support the diabetes management is stored in the databases, the risk associated with a database failure is magnified in this context, as opposed to risk associated with data in a mobile phone or mp3 player becoming corrupted. Thus, to reduce the risk that medically important data is not corrupted, the disclosed handheld diabetes manager includes a database management application that maintains a plurality of databases, wherein the databases are separated based upon (i) the frequency at which the database is updated and/or indexed and (ii) the criticality of the records stored therein.

For example, it is appreciated that the frequency at which CGM measurements are taken by the CGM, (e.g., every five minutes), can be much greater than the frequency at which a blood glucose measurement is obtained using the blood glucose reader, e.g., 4 or 5 times a day. Further, to enable a patient to better monitor his or her blood glucose between readings from the blood glucose reader, it is beneficial to store the CGM measurements in a database. As discussed, however, the CGM measurements are not used to make medical decisions, i.e., how much insulin to include in a bolus, while the blood glucose readings from the blood glucose reader are used to make medical decisions. Therefore, the blood glucose measurement records are more critical to the patient's diabetes management than the CGM records. To ensure that updating a database with a new CGM record does not cause the failure of the database storing the blood glucose measurement records, the CGM records are stored in a different database than the database storing the blood glucose measurement records.

As will be discussed, the database management application can be further configured to detect when a database has failed or a record stored therein has been corrupted.

Figure 6:
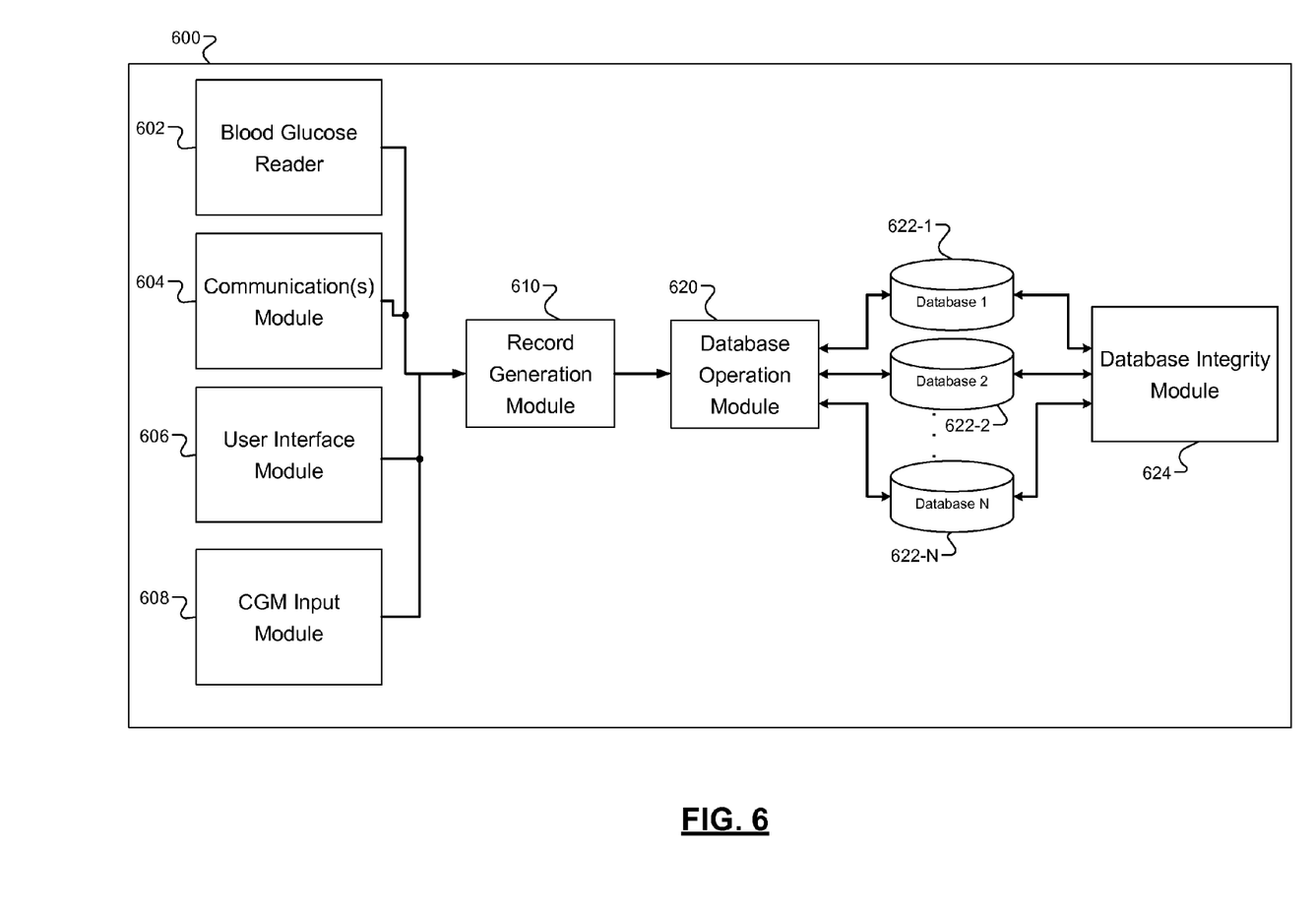
FIG. 6 shows a component level architecture of a database management system of a diabetes management device.

FIG. 6 illustrates exemplary components of a diabetes manager 600 configured to solve the technical problem identified above. The diabetes manager 600 includes a plurality of input modules. In an exemplary embodiment, the input modules of the diabetes manager 600 may include but are not limited to a blood glucose reader 602, one or more communications modules 604, a user interface module 606, and a CGM input module 608. The various input modules can be configured to output data to a record generator 610, that generates a new record for storage in at least one of a plurality of databases 622-1, 622-2, ... 622-N. The new record will have a corresponding record type, e.g., a blood glucose measurement record or an error record. The new record is communicated to a database operation module 620, which is configured to operate on the plurality of databases 622-1-622-N such that the database operation module 620 updates one of the databases with the new record. A database integrity module 624 analyzes the databases 622-1-622-N to ensure that the databases have not failed.

The diabetes manager 600 includes a blood glucose reader 602. The blood glucose reader 602 receives a fluid sample from a patient and outputs a blood glucose measurement based on the fluid sample. For instance, the blood glucose reader 602 can include a blood glucose measurement engine that receives a test strip containing a small amount of the patient's bodily fluid, e.g., a drop of blood, and that determines an amount of glucose in the blood therefrom. The blood glucose reader 602 may be integrated into the housing of the diabetes manager such that the patient deposits the fluid sample on the strip and inserts the test strip into the blood glucose reader. The blood glucose reader 602 outputs a blood glucose measurement which is used to generate a blood glucose measurement record. As will be discussed, the blood glucose measurement record is generated by the record generation module 610 based on the blood glucose measurement and is communicated to the database operation module 620.

The communication module(s) 604 can be any of the communication interfaces discussed above. An exemplary communication module may be a Bluetooth® receiver which is in wireless communication with an external device, e.g., an insulin pump. It is appreciated that the diabetes manager 600 may include more than one communications modules 604 depending on how many communications protocols are enabled on the device. In addition to supporting Bluetooth® communications, an exemplary communication module may support infra red (IR) communications, radio frequency (RF) communications, or any other wireless communications. Further, an exemplary communications module may support wireline communications, such as those received via a USB interface or a LAN interface. An exemplary communications module may receive data from the external device and metadata which provides information including but not limited to a time-stamp and/or a device identifier.

In an exemplary embodiment, the user interface 606 is a touch screen adapted to receive a patient's input. The patient can use the user interface 606 to enter patient data, such as meal information and personal information. While a touch screen is considered, it is appreciated that other user interfaces are contemplated. For example, a display and a small keyboard integrated on the diabetes manager 600 can be used to enter patient data as well. The user interface 606 receives user input and generates data indicating the same. The data is communicated to the record generation module 610, which generates a new record based thereon.

The CGM input module 608 is configured to receive CGM measurements from a CGM. In a preferred embodiment, the CGM input module 608 utilizes a proprietary Gazell wireless protocol developed by Nordic Semiconductor, Inc. It is appreciated that in other embodiments, the CGM input module 608 may be a wireless interface such as Bluetooth®, IR, or RF, or a wireline interface. The CGM measurements are received by the CGM input module 608 and communicated to the record generation module 610. It is appreciated that some CGMs may not generate metadata and may only provide CGM measurements. In this scenario, the CGM input module 608 may generate metadata tags by applying a timestamp or other metadata to the raw CGM measurements.

The record generation module 610 is configured to generate records for storage in the N databases 622-1-622-N. Based on the type of data received, the record generation module 610 can generate a record having a record type. Depending on the record type being generated, the record generation module 610 can fill in different fields of the record with data received from one or more of the input modules 602-608. For instance, if a new blood glucose measurement is received from the blood glucose reader 602, the record generation module 610 can generate a blood glucose measurement record. A blood glucose measurement record, however, may include meal information such as an amount of carbohydrates consumed in a recent meal or an amount of carbohydrates to be consumed in an upcoming meal, which is received via the user interface 606.

Furthermore, the record generation module 610 can also include a time stamp and a record identifier in the new record. Additionally, the record generation module 610 calculates a cyclic redundancy check (CRC) and/or a checksum using predetermined functions. The calculated CRC and/or checksum values is/are inserted into a newly generated record.

An exemplary record entry is provided herein:
New Blood Glucose Measurement Record{

Record_ID;
Year_of_Measurement;
Month_of_Measurement;
Day_of_Measurement;
Time_of_Measurement;
bG_measurement;
...
Amount_of_carbs_before_measurement;
Food_item;
...
CRC value;
}

It is appreciated that a separate record generation module 610 may be integrated into each input module 602-608 such that when data is received from a data source, the respective input module generates the new record.

The database operation module 620 is configured to perform database operations on the N databases 622-1-622-N. Database operations include but are not limited to creating, deleting, and/or updating a database. Updating a database includes inserting a new record generated by the record generation module 620 into the appropriate table of an appropriate database. The database operations module 620 can also perform indexing of the databases. Each database of the N databases 622-1-622-N may have a corresponding index. The size of the index for a particular database can be adjusted based on how frequently the database is searched or read from. The database operation module 620 can be further configured to perform operations such as reads and searches.

The N databases 722-1-722-N are now described in greater detail. The N databases 722-1-722-N have a different frequency ranges associated thereto. A new record of a particular record type received from one of the blood glucose reader, the user interface, and the communication interface is stored in a particular database of the N databases based on the frequency range of the particular database and the frequency of the particular record type. Each database includes at least one table and at least one index for the database. A table is comprised of a set of records of the same record type. For instance, each time a patient's blood glucose levels are measured by the blood glucose reader, a blood glucose measurement can be stored in a blood glucose measurement table. An index is a database table attribute which can be used to decrease search times. Indexes can be created for any field within the table, primarily for fields which searches are frequently performed.

Figure 7B:
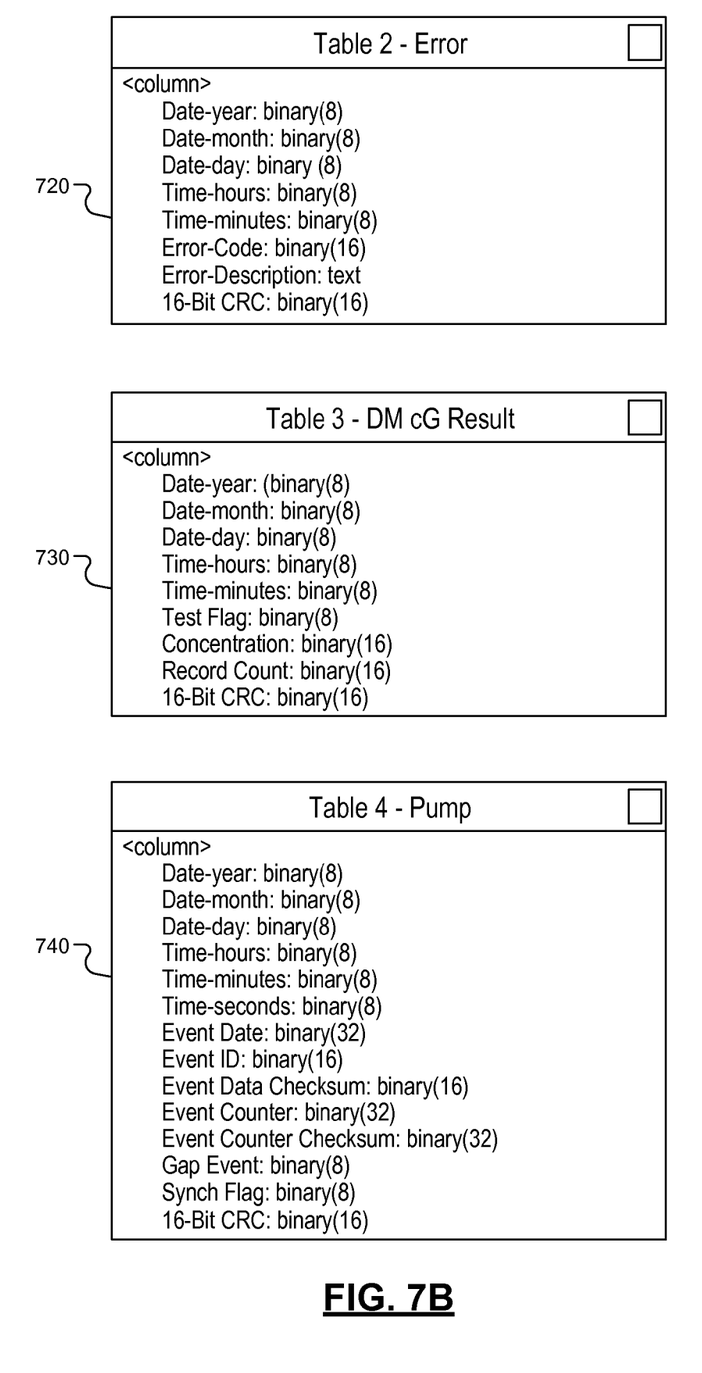
Figure 7C:
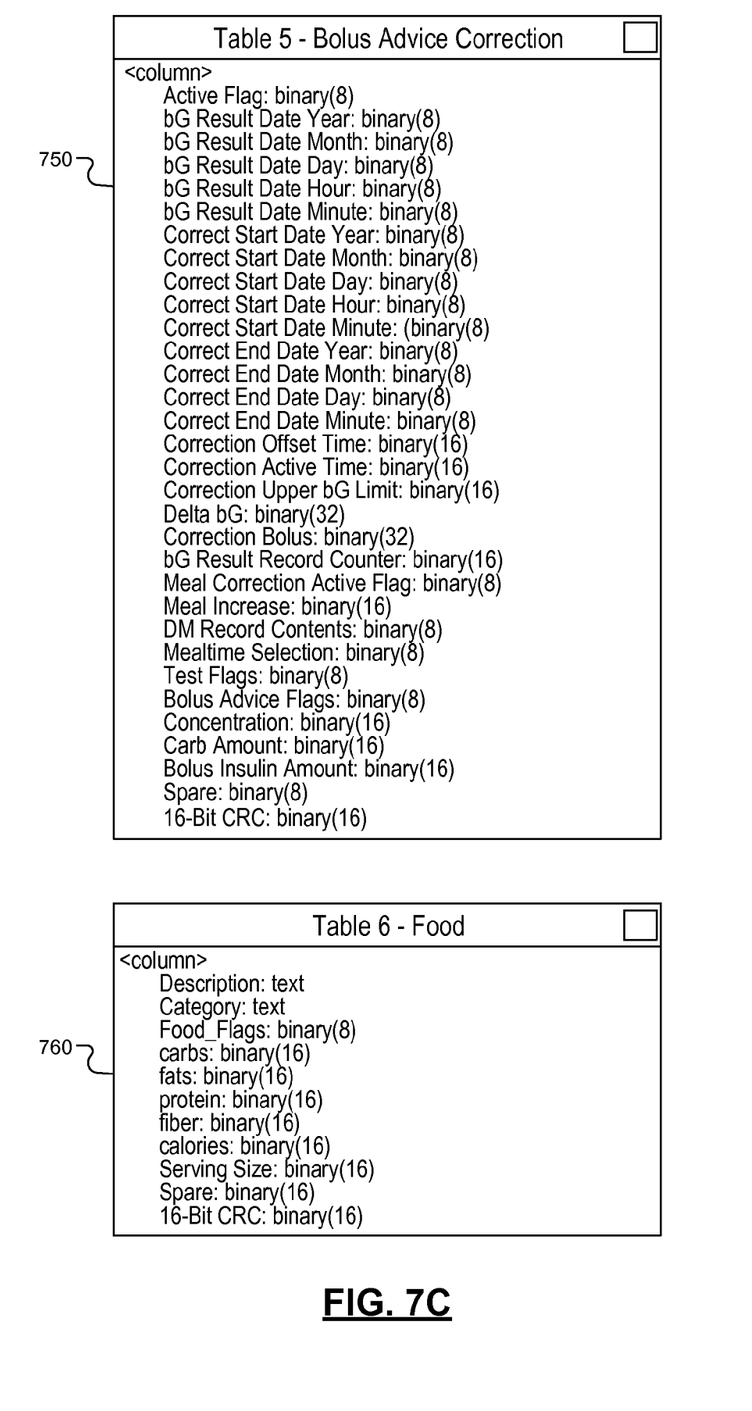

FIGS. 7A-C illustrate exemplary tables that comprise the N databases. Table 710 is an exemplary table for storing diabetes manager results. Included in the table are columns or fields for, inter alia, for: i) time stamp information include a year, month, day, hour, minute, and second of a result, ii) blood glucose measurement test results including a test flag, a blood glucose reading, and a record count, iii) meal information, iv) bolus information, and v) a cyclic redundancy check (CRC) value. Table 720 stores error records relating to operational errors that may have been detected in the system of devices. Table 730 stores records relating to the results of the CGM. Table 740 stores pump records relating to the insulin pump in communication with the diabetes manager. Table 750 stores bolus correction records relating to the bolus advice correction. Table 760 stores meal records relating to a patient's food intake.

Each record entry can include a cyclic redundancy check (CRC) value. As will be discussed below, the CRC value is used to verify the integrity of the record, the table, or the database. Furthermore, some tables, such as table 740, may include a checksum value as additional verification that the record is uncorrupted.

It is appreciated that the foregoing tables, and the contents stored therein, are exemplary and are only meant to demonstrate the types of data that may be stored in a table. It is noted that one or more of the tables are relational to one another. Furthermore, the relations may extend from a first database 622-I to a second database 622-M. For instance, the blood glucose measurement field in table 710 may be related to a CGM measurement field in another table via the respective time stamp fields in the tables.

Referring to FIGS. 6 and 7A-C in combination, the N databases 622-1-622-N are separated based upon a frequency range and criticality of the records stored therein. Using the exemplary tables provided in FIGS. 7A-C, an example of the division of the databases 622-1-622-N is provided, where N is four. Database 622-1 stores records that are recorded more than 25 times/day and are critical to a patient's diabetes management. Database 622-2 stores records that are recorded more than 25 times/day but are not critical to the patient's diabetes management. Database 622-3 stores records that are recorded 25 times/day or less and are critical to a patient's diabetes management. Database 622-4 stores records that are recorded 25 times/day or less and are not critical to a patient's diabetes management.

As mentioned table 730 stores the CGM records, which may be received every 5 minutes or 480 records/day. The CGM records can be used to provide a graphical display to the patient on a display associated with the diabetes manager 600. The CGM records are not used, however, to make medical decisions such as how much insulin to deliver in the bolus. Thus, the CGM records are considered to be of lower criticality. In this example, table 730 is stored in database 622-2 because CGM records are received at a frequency which is greater than 25 times/day and are not critical to the patient's diabetes management. Thus, when a new CGM record is received via the CGM input module 608, the database operation module 620 updates database 722-2 by adding the new CGM record to table 730.

An insulin pump may deliver a bolus to the patient between 3 and 5 times a day. When a bolus is delivered, data relating to whether the bolus was successfully delivered may be received via the communications module 604. Based thereon, a pump record may be generated. As pump records are critical to a patient's treatment and new pump records are received less than 25 times/day, table 740 is stored in database 622-3. When a new pump record is received via the communications module 604, the database operation module 620 updates database 722-3 by adding the new CGM record to table 730.

Referring back to FIG. 6, the database application of the exemplary diabetes manager 600 includes an integrity check module that performs an integrity check on a critical database of the N databases to determine if a critical record in the critical database has been corrupted. The database application is configured to ensure that each database have the following properties: atomicity, consistency, isolation, durability (ACID). In an exemplary embodiment, Microsoft Sequel CE® is configured to ensure that these properties are adhered to. As mentioned, however, the databases reside on a non-volatile solid-state memory. Thus, in the operational lifetime of the diabetes manager 600, a portion of the memory may fail. In these instances, a failure may be as simple as a single bit value being flipped. To ensure that a record has not been corrupted, the integrity check module 624 performs integrity checks on the records in each database by determining if a critical record has been corrupted by calculating a check value based on the critical record and comparing it to a stored check value that was previously calculated based on the critical record at a time that the critical record was stored in the critical database. As mentioned, the record generation module 610 inserts at least one of a CRC value and a checksum value in a new record. The CRC value or the checksum is calculated by a predetermined function that receives values indicative of the data entered into the fields of the record. The integrity check module 624 use the same formula and the same fields to generate a CRC check value or a checksum check value as the record generation module 610 uses to generate the CRC value and or the checksum value. If the CRC check value or checksum check value matches the CRC value or the checksum value stored in the record, then the integrity module 624 checks the next record. If, however, the check value does not match the stored value, the integrity check module 624 will deem the record corrupted. A bit flag in the record may be switched to indicate that the record has been corrupted. A corrupted record can be removed from its respective database or the database itself can be deleted and rebuilt. Furthermore, in some embodiments where storage space and computational resources are not primary concerns, database mirroring may be performed such that a failed database can be recreated using the mirror copy of the database.

In an aspect of the disclosure, a handheld diabetes management device having a database management system is disclosed. The handheld diabetes management device includes a blood glucose reader that receives a fluid sample from a patient and that outputs a blood glucose measurement that is used to generate a first record having a first record type, a user interface that receives input from the patient via an input device associated with the handheld diabetes management device and that outputs patient data that is used to generate a second record having a second record type, a communication interface that receives data from an external device and that outputs device data that is used to generate a third record having a third record type. The first record type, the second record type, and the third record type are of a plurality of different record types. Each record type of the plurality of different record types has a corresponding frequency. The frequency of a record type indicates an average amount of records having the record type received during a predetermined period of time; N databases each having a different frequency range associated thereto. A new record of a particular record type based on data received from one of the blood glucose reader, the user interface, and the communication interface is stored in a particular database of the N databases based on the frequency range of the particular database and the frequency of the particular record type, where N is an integer greater than 1. The handheld diabetes management device further includes a database operation module that performs database operations on the N databases.

In another feature, the diabetes management device further includes a database integrity module that performs an integrity check on a critical database of the N databases to determine if a critical record in the critical database has been corrupted.

In another feature, the database integrity module determines if the critical record has been corrupted by calculating a check value based on the critical record and comparing it to a stored check value that was previously calculated based on the critical record at a time when the critical record was stored in the critical database. A predetermined function is used to calculate the check value and the stored check value.

In another feature, the database integrity module further includes a continuous blood glucose input module that receives a blood glucose reading from a continuous blood glucose meter and outputs a continuous blood glucose measurement used to generate a fourth record of a fourth record type. The fourth record is stored in a different database of the N databases than a database storing the first records.

In another feature, each of the N databases includes an index and at least one table. A table stores records of a corresponding record type.

In another feature, at least a first record in a first table of a first database has a relationship to a second record in a second table of a second database.

In another feature, the relationship between the first record and the second record is based on a time stamp of both the first record and the second record.

In another feature, the diabetes management device further includes a record generation module that receives data and that generates the new record having the particular record type based on the received data.

In another aspect of the disclosure, a handheld diabetes management device having a database management system is disclosed. The handheld diabetes management devices includes a plurality of input modules, the plurality of modules including i) a blood glucose reader that receives a fluid sample from a patient and that outputs a blood glucose measurement that is used to generate a first record having a first record type; ii) a user interface that receives input from the patient via an input device associated with the handheld diabetes management device and that outputs patient data that is used to generate a second record having a second record type; iii) a communication interface that receives data from an external device and that outputs device data that is used to generate a third record having a third record type; and iv) a continuous blood glucose input module that receives a blood glucose reading from a continuous blood glucose meter and that outputs a continuous blood glucose measurements used to generate a fourth record of a fourth record type. The first record type, the second record type, the third record type, and the fourth record type are of a plurality of different record types. Each record type of the plurality of different record types has a corresponding frequency. The frequency of a record type indicates an average amount of records having the record type received during a predetermined period of time. The diabetes management device further includes a record generation module that receives data from one or more of the input modules and that generates a new record of a particular record type based on the received data; N databases each having a different frequency range associated thereto. A new record is stored in a particular database of the N databases based on the frequency range of the particular database and the frequency of the particular record type, where N is an integer greater than 1. The diabetes management device further includes a database operation module that performs database operations on the N databases.

In another feature, the diabetes management device further includes a database integrity module that performs an integrity check on a critical database of the N databases to determine if a critical record in the critical database has been corrupted.

In another feature, the database integrity module determines if the critical record has been corrupted by calculating a check value based on the critical record and comparing it to a stored check value that was previously calculated based on the critical record at a time when the critical record was stored in the critical database. A predetermined function is used to calculate the check value and the stored check value.

In another feature, each of the N databases includes an index and at least one table. A table stores records of a corresponding record type.

In another feature, at least a first record in a first table of a first database has a relationship to a second record in a second table of a second database.

In another feature, the relationship between the first record and the second record is based on a time stamp of both the first record and the second record.

In another feature, the first records are stored in a first database and the fourth records are stored in a second database, whereby if the second database fails the first records are preserved.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

What is claimed is:

1. A handheld diabetes management device having a database management system comprising:
    a blood glucose reader that receives a fluid sample from a patient and that outputs a blood glucose measurement that is used to generate a first record having a first record type;
    a user interface that receives input from the patient via an input device associated with the handheld diabetes management device and that outputs patient data that is used to generate a second record having a second record type;
    a communication interface that receives data from an external device and that outputs device data that is used to generate a third record having a third record type, wherein the first record type, the second record type, and the third record type are ones of a plurality of different record types, wherein each record type of the plurality of different record types has a corresponding frequency, wherein the frequency of a record type indicates an average amount of records having the record type received during a predetermined period of time;
    N databases each having a different frequency range associated thereto, wherein a new record of a particular record type based on data received from one of the blood glucose reader, the user interface, and the communication interface is stored in a particular database of the N databases based on the frequency range of the particular database and the frequency of the particular record type, and wherein N is an integer greater than 1; and
    a database operation module that performs database operations on the N databases.

2. The handheld diabetes management device of claim 1 further comprising a database integrity module that performs an integrity check on a critical database of the N databases to determine if a critical record in the critical database has been corrupted.

3. The handheld diabetes management device of claim 2 wherein the database integrity module determines if the critical record has been corrupted by calculating a check value based on the critical record and comparing it to a stored check value that was previously calculated based on the critical record at a time when the critical record was stored in the critical database, wherein a predetermined function is used to calculate the check value and the stored check value.

4. The handheld diabetes management device of claim 1 further comprising a continuous blood glucose input module that receives a blood glucose reading from a continuous blood glucose meter and outputs a continuous blood glucose measurement used to generate a fourth record of a fourth record type, wherein the fourth record is stored in a different database of the N databases than a database storing the first records.

5. The handheld diabetes management device of claim 1 wherein each of the N databases comprises an index and at least one table, wherein a table stores records of a corresponding record type.

6. The handheld diabetes management device of claim 5 wherein at least a first record in a first table of a first database has a relationship to a second record in a second table of a second database.

7. The handheld diabetes management device of claim 6 wherein the relationship between the first record and the second record is based on a time stamp of both the first record and the second record.

8. The handheld diabetes management device of claim 1 further comprising a record generation module that receives data and that generates the new record having the particular record type based on the received data.

9. A handheld diabetes management device having a database management system comprising:
 a plurality of input modules, the plurality of modules including
  i) a blood glucose reader that receives a fluid sample from a patient and that outputs a blood glucose measurement that is used to generate a first record having a first record type;
  ii) a user interface that receives input from the patient via an input device associated with the handheld diabetes management device and that outputs patient data that is used to generate a second record having a second record type;
  iii) a communication interface that receives data from an external device and that outputs device data that is used to generate a third record having a third record type; and
  iv) a continuous blood glucose input module that receives a blood glucose reading from a continuous blood glucose meter and that outputs a continuous blood glucose measurements used to generate a fourth record of a fourth record type;
 wherein the first record type, the second record type, the third record type, and the fourth record type are ones of a plurality of different record types, wherein each record type of the plurality of different record types has a corresponding frequency, wherein the frequency of a record type indicates an average amount of records having the record type received during a predetermined period of time;
 a record generation module that receives data from one or more of the input modules and that generates a new record of a particular record type based on the received data;
 N databases each having a different frequency range associated thereto, wherein a new record is stored in a particular database of the N databases based on the frequency range of the particular database and the frequency of the particular record type, where N is an integer greater than 1; and
 a database operation module that performs database operations on the N databases.

10. The handheld diabetes management device of claim 9 further comprising a database integrity module that performs an integrity check on a critical database of the N databases to determine if a critical record in the critical database has been corrupted.

11. The handheld diabetes management device of claim 10 wherein the database integrity module determines if the critical record has been corrupted by calculating a check value based on the critical record and comparing it to a stored check value that was previously calculated based on the critical record at a time that the critical record was stored in the critical database, wherein a predetermined function is used to calculate the check value and the stored check value.

12. The handheld diabetes management device of claim 9 wherein each of the N databases comprises an index and at least one table, wherein a table stores records of a corresponding record type.

13. The handheld diabetes management device of claim 12 wherein at least a first record in a first table of a first database has a relationship to a second record in a second table of a second database.

14. The handheld diabetes management device of claim 13 wherein the relationship between the first record and the second record is based on a time stamp of both the one record and the another record.

15. The handheld diabetes management device of claim 12 wherein the first records are stored in a first database and the fourth records are stored in a second database, whereby if the second database fails the first records are preserved.

* * * * *

UNITED STATES PATENT AND TRADEMARK OFFICE
CERTIFICATE OF CORRECTION

PATENT NO. : 8,494,607 B2  
APPLICATION NO. : 12/905475  
DATED : July 23, 2013  
INVENTOR(S) : Sabo et al.

It is certified that error appears in the above-identified patent and that said Letters Patent is hereby corrected as shown below:

In the Specifications

Column 10, line 4, delete "722-1-722-N" and insert --622-1-622-N--.

Column 10, line 5, delete "722-1-722-N" and insert --622-1-622-N--.

Column 11, line 10, delete "722-2" and insert --622-2--.

Column 11, line 21, delete "722-3" and insert --622-3--.

Column 11, line 21, delete "730" and insert --740--.

Signed and Sealed this  
Twenty-fourth Day of December, 2013

Margaret A. Focarino  
*Commissioner for Patents of the United States Patent and Trademark Office*